(12) United States Patent
Thallapuranam et al.

(10) Patent No.: US 9,556,226 B2
(45) Date of Patent: Jan. 31, 2017

(54) PEPTIDES WITH ANTIFUNGAL ACTIVITY AND METHODS OF USING THE PEPTIDES

(71) Applicant: THE BOARD OF TRUSTEES OF THE UNIVERSITY OF ARKANSAS, Little Rock, AR (US)

(72) Inventors: Suresh Kumar Thallapuranam, Fayetteville, AR (US); David S. McNabb, Fayetteville, AR (US); Yazan Hussien Akkam, Fayetteville, AR (US); Duy Tu Nguyen, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 14/777,321

(22) PCT Filed: Mar. 14, 2014

(86) PCT No.: PCT/US2014/028229
§ 371 (c)(1),
(2) Date: Sep. 15, 2015

(87) PCT Pub. No.: WO2014/144004
PCT Pub. Date: Sep. 18, 2014

(65) Prior Publication Data
US 2016/0039873 A1 Feb. 11, 2016

Related U.S. Application Data

(60) Provisional application No. 61/789,307, filed on Mar. 15, 2013.

(51) Int. Cl.
| | | |
|---|---|---|
| *A61K 38/04* | (2006.01) | |
| *A61K 38/08* | (2006.01) | |
| *A61K 38/12* | (2006.01) | |
| *C07K 7/06* | (2006.01) | |
| *C07K 7/08* | (2006.01) | |
| *C07K 14/47* | (2006.01) | |
| *A01N 37/46* | (2006.01) | |
| *A01N 47/44* | (2006.01) | |
| *A01N 37/18* | (2006.01) | |

(52) U.S. Cl.
CPC .............. *C07K 7/06* (2013.01); *A01N 37/18* (2013.01); *A01N 37/46* (2013.01); *A01N 47/44* (2013.01); *A61K 38/04* (2013.01); *A61K 38/08* (2013.01); *A61K 38/12* (2013.01); *C07K 7/08* (2013.01); *C07K 14/4723* (2013.01)

(58) Field of Classification Search
CPC ........ A61K 38/04; A61K 38/08; A61K 38/12; C07K 14/4723; C07K 7/06; C07K 7/08
USPC .... 514/3.3, 3.4, 3.5; 530/327, 328, 329, 330
See application file for complete search history.

(56) References Cited

U.S. PATENT DOCUMENTS

| | | |
|---|---|---|
| 4,725,576 A | 2/1988 | Pollock et al. |
| 5,486,503 A | 1/1996 | Oppenheim et al. |
| 5,696,078 A | 12/1997 | Oppenheim et al. |
| 5,885,965 A | 3/1999 | Oppenheim |
| 5,912,230 A | 6/1999 | Oppenheim et al. |
| 6,309,669 B1 | 10/2001 | Setterstrom et al. |
| 6,528,488 B2 | 3/2003 | Spacciapoli et al. |
| 6,531,573 B1 | 3/2003 | Oppenheim et al. |
| 6,555,650 B1 | 4/2003 | Lajoie |
| 6,576,226 B1 | 6/2003 | Jernberg |
| 6,638,531 B1 | 10/2003 | Van Nieuw Amerongen et al. |
| 7,271,239 B2 | 9/2007 | Bobek |
| 7,569,542 B2 | 8/2009 | Eckert et al. |
| 7,601,361 B2 | 10/2009 | Lu et al. |
| 9,029,636 B2 * | 5/2015 | Wu ............ C07K 14/415 435/419 |
| 2003/0143234 A1 | 7/2003 | Shi et al. |
| 2006/0069022 A1 | 3/2006 | Bobek |
| 2008/0170991 A1 | 7/2008 | Shi et al. |
| 2009/0143295 A1 | 6/2009 | O'Brien |
| 2009/0233074 A1 | 9/2009 | Haynie |
| 2009/0312265 A1 | 12/2009 | Schmidtchen et al. |
| 2009/0325866 A1 | 12/2009 | Kim |
| 2010/0143876 A1 | 6/2010 | Murphy |
| 2010/0173833 A1 | 7/2010 | Lajoie |
| 2010/0184654 A1 | 7/2010 | Eckert et al. |
| 2010/0202983 A1 | 8/2010 | Jernberg |

(Continued)

FOREIGN PATENT DOCUMENTS

| | | |
|---|---|---|
| WO | 9640770 | 12/1996 |
| WO | 0001427 | 1/2000 |

(Continued)

OTHER PUBLICATIONS

Akkam, Yazan, thesis: "Design, Development, and Characterization of Novel Antimicrobial Peptides for Pharmaceutical Applications", University of Arkansas, Aug. 2013.

(Continued)

*Primary Examiner* — Julie Ha
(74) *Attorney, Agent, or Firm* — Andrus Intellectual Property Law, LLP

(57) ABSTRACT

Compositions with antifungal activity and methods of using such compositions are provided herein. In particular the compositions are peptides of SEQ ID NO: 1 and variations thereof. The peptides may contain L or D amino acids and may be circularized, dimerized or otherwise modified to make the compositions resistant to proteolysis. The compositions may be used to inhibit microbial growth and in particular fungal growth.

15 Claims, 11 Drawing Sheets

(56) References Cited

U.S. PATENT DOCUMENTS

2012/0065401 A1* 3/2012 Grainger .............. A61K 31/13 546/54
2013/0332133 A1* 12/2013 Horn ..................... C12N 9/00 703/11

FOREIGN PATENT DOCUMENTS

| WO | 0032629 | 6/2000 |
| WO | 0156627 | 8/2001 |

OTHER PUBLICATIONS

Brewer, H. Hunter, G. Lajoie, NMR studies of the antimicrobial salivary peptides histatin 3 and histatin 5 in aqueous and nonaqueous solutions, Biochemistry and cell biology = Biochimie et biologie cellulaire 76 (1998) 247-256.

Duke, Hannah, thesis: "A Comparison of Retro and Wild Type Antifungal Peptides Based on Structure and Function", University of Arkansas, Apr. 15, 2009.

Duke, Hannah, et al., poster presentation: "A Comparison of Retro and Wild Type Antifungal Peptides Based on Structure and Function", University of Arkansas, Apr. 15, 2009.

Edgerton, S.E. Koshlukova, T.E. Lo, B.G. Chrzan, R.M. Straubinger, P.A. Raj, Candidacidal activity of salivary histatins. Identification of a histatin 5-binding protein on Candida albicans, The Journal of biological chemistry 273 (1998) 20438-20447.

Edgerton, S.E. Koshlukova, Salivary histatin 5 and its similarities to the other antimicrobial proteins in human saliva, Advances in dental research 14 (2000) 16-21.

Gyurko, U. Lendenmann, R.F. Troxler, F.G. Oppenheim, Candida albicans mutants deficient in respiration are resistant to the small cationic salivary antimicrobial peptide histatin 5, Antimicrobial agents and chemotherapy 44 (2000) 348-354.

Helmerhorst, P. Breeuwer, W. van't Hof, E. Walgreen-Weterings, L.C. Oomen, E.C. Veerman, A.V. Amerongen, T. Abee, The cellular target of histatin 5 on Candida albicans is the energized mitochondrion, The Journal of biological chemistry 274 (1999) 7286-7291.

Jang, X.S. Li, J.N. Sun, M. Edgerton, The P-113 fragment of histatin 5 requires a specific peptide sequence for intracellular translocation in Candida albicans, which is independent of cell wall binding, Antimicrobial agents and chemotherapy 52 (2008) 497-504.

Li, J.N. Sun, K. Okamoto-Shibayama, M. Edgerton, Candida albicans cell wall ssa proteins bind and facilitate import of salivary histatin 5 required for toxicity, The Journal of biological chemistry 281 (2006) 22453-22463.

Luque-Ortega, W. van't Hof, E.C. Veerman, J.M. Saugar, L. Rivas, Human antimicrobial peptide histatin 5 is a cell-penetrating peptide targeting mitochondrial ATP synthesis in Leishmania, Faseb J 22 (2008) 1817-1828.

Melino, S. Rufini, M. Sette, R. Morero, A. Grottesi, M. Paci, R. Petruzzelli, Zn(2+) ions selectively induce antimicrobial salivary peptide histatin-5 to fuse negatively charged vesicles. Identification and characterization of a zinc-binding motif present in the functional domain, Biochemistry 38 (1999) 9626-9633.

Moutos, Christopher, thesis: "Membrane Permeability Induced by Stereo and Retro Analogs of Histatin 5", University of Arkansas, May 2013.

Nguyen, Duy T., thesis: "Development of Novel Antifungal Peptides Based on a Natural Model of Histatin-5 Peptide", University of Arkansas, Dec. 2013.

Raj, S.D. Soni, M.J. Levine, Membrane-induced helical conformation of an active candidacidal fragment of salivary histatins, The Journal of biological chemistry 269 (1994) 9610-9619.

Veerman, K. Nazmi, W. Van't Hof, J.G. Bolscher, A.L. Den Hertog, A.V. Nieuw Amerongen, Reactive oxygen species play no role in the candidacidal activity of the salivary antimicrobial peptide histatin 5, The Biochemical journal 381 (2004) 447-452.

Yamagishi, D.H. Fitzgerald, T. Sein, T.J. Walsh, B.C. O'Connell, Saliva affects the antifungal activity of exogenously added histatin 3 towards Candida albicans, FEMS microbiology letters 244 (2005) 207-212.

Ku, S.M. Levitz, R.D. Diamond, F.G. Oppenheim, Anticandidal activity of major human salivary histatins, Infection and Immunity 59 (1991) 2549-2554.

International Search Report and Written Opinion for International Application No. PCT/US2014/028229, dated Jul. 3, 2014 (11 pages).

* cited by examiner

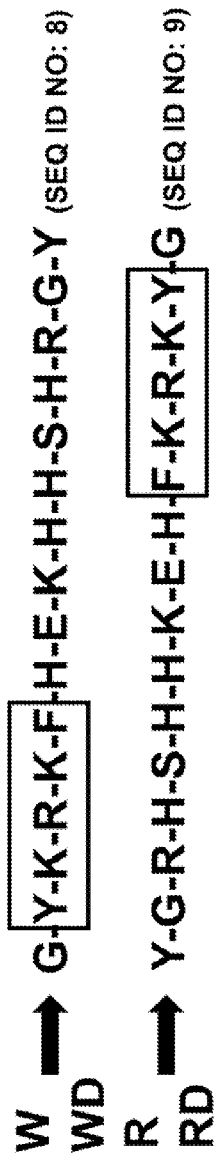
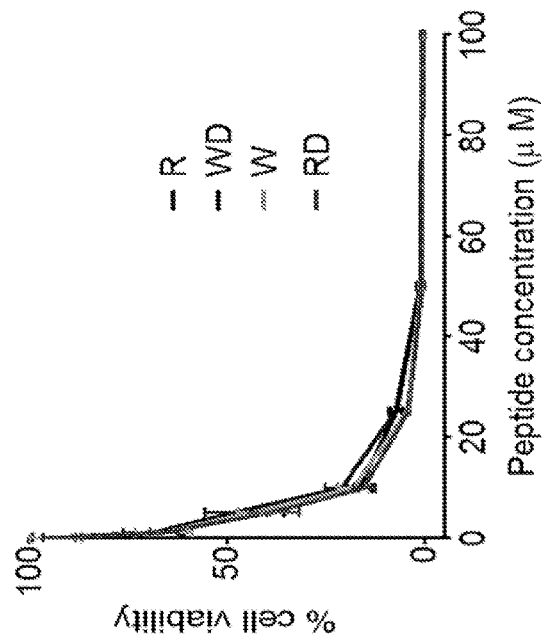

PEPTIDES WITH ANTIFUNGAL ACTIVITY AND METHODS OF USING THE PEPTIDES

CROSS-REFERENCE TO RELATED APPLICATIONS

This patent application is a national stage filing under 35 U.S.C. 371 of International Application No. PCT/US2014/028229, filed Mar. 14, 2014, which claims the benefit of priority of U.S. Provisional Patent Application No. 61/789,307, filed Mar. 15, 2013, both of which are incorporated herein by reference in their entirety.

STATEMENT REGARDING FEDERALLY SPONSORED RESEARCH

This invention was made with United States government support awarded by the National Institutes of Health grant numbers 1P30RR031154 and P30 GM 103450. The United States may have certain rights in this invention.

SEQUENCE LISTING

This application is being filed electronically via EFS-Web and includes an electronically submitted Sequence Listing in .txt format. The .txt file contains a sequence listing entitled "2014-03-14_5965-00039_ST25.txt" created on Mar. 14, 2014 and is 5782 bytes in size. The Sequence Listing contained in this .txt file is part of the specification and is hereby incorporated by reference herein in its entirety.

INTRODUCTION

Fungi have emerged worldwide as an increasingly frequent cause of opportunistic infections. A survey of the epidemiology of sepsis in the United States reveals that the incidence of fungal sepsis increased three-fold between 1979 and 2000. *Candida* and *Aspergillus* spp. are the most frequent causes of invasive fungal infections and are frequently associated with high morbidity and mortality. The rate of invasive *candidiasis* is 7 to 15-fold higher than *aspergillosis*. In fact, *Candida* is the fourth leading microorganism responsible for bloodstream infections in the United States. In recent decades, there has been a shift in the epidemiology of *Candida* infections, characterized by a progressive move from the predominance of *Candida albicans* toward non-albicans *Candida* spp. such a *Candida glabrata* and *Candida krusesi*. In fact, *C. glabrata* now accounts for 15% to 20% of *Candida* infections in most countries.

In intensive care unit patients, the most common types of *Candida* infections are bloodstream infections, catheter-related infections, intra-abdominal infections and urinary tract infections. Invasive candidiasis is a leading cause of morbidity and mortality in both immunocompromised and immunocompetent critically ill patients with a mortality rate between 20% and 40%. The current antifungal chemotherapies are predominantly three major groups of compounds: the polyenes, the azoles, and the echinocandins. Some strains of *Candido* have acquired resistance to the azoles while other *Candida* species, such as *C. glabrata* or *C. krusei* are not azole-sensitive at typical therapeutic concentrations. In contrast, the polyenes (e.g. amphotericin B) remain highly effective; however, drug toxicity has limited its usage in systemic infections. The echinocandins have proven useful, but resistance to these drugs is also observed via mutations in the FKS1 gene. Thus, there is an intensive effort to identify new antifungals that would be effective against a broad range of *Candida* species as well as other pathogenic fungi.

SUMMARY

Novel antimicrobial and in particular anti-fungal peptide compositions are provided herein. The compositions include a five amino acid peptide of SEQ ID NO: 1 (W/F/Y-K-R-K-F/Y/W). The peptides are antifungal when produced using either D or L amino acids and has similar antifungal activity when made in a retro or reverse form. Anti-fungal activity was increased when the peptide was dimerized via a cysteine added to either the N or C terminal end of the peptide. The peptide may be dimerized or circularized through disulphide bonds between the cysteine residues. Pie peptides may also be circularized via other methods such as an amide bond between the N- and C-terminal end. The N-terminal amino acid can be substituted with a methionine or a methionine residue can be added to the N-terminus to facilitate circularization. The peptides may also be produced as a nine or ten amino acid duplicated peptide (i.e. F/Y-K-R-K -F/Y-K-R-K-F/Y (SEQ ID NO: 6) or F/Y-K-R-K-F/Y-K-R-K-F/Y (SEQ ID NO: 7)).

The peptides have anti-fungal activity both in vitro and in vivo. In one aspect, the compositions may be used in methods of inhibiting microbial infections or microbial contamination. The compositions comprising the peptides described herein may be administered to a subject in need of treatment for a microbial infection and may inhibit the growth of the microbe, prevent further spread of the microbe or kill the microbe and cure or stop the infection.

In another aspect, the compositions may be applied to a surface such as a countertop, a food item or a food preparation surface to reduce the chance of microbial or in particular fungal infection. In yet another aspect, the compositions may be added to a liquid such as a drink or media for growing cells to inhibit microbial growth, in particular to inhibit fungal growth. In a still further aspect, methods of inhibiting microbial growth by contacting cells with the compositions described, herein to prevent microbial growth in, on or with the cells are provided.

BRIEF DESCRIPTION OF THE DRAWINGS

FIG. 1 is a schematic depiction of the sequence of the histatin 5 16mer derivative (W; SEQ ID NO: 8) and the retro-histatin 5 16 mer (R; SEQ ID NO: 9). The same peptides were generated using both L-amino acids (W and R) and D-amino acids (WD and RD), respectively.

FIG. 2 is a graph and table showing the antifungal activity of the histatin 5 16mer derivatives. FIG. 2A shows the percent viability of *Candida albicans* SC5314 following exposure to increasing concentrations of the four histatin 5 16mer peptide derivatives. FIG. 2B is a table summarizing the dose of peptide required to achieve 50% killing activity ($LD_{50}$) of *C. albicans* SC5314 with each of the peptides. The W, WD, R and RD designates the wild-type (W) or retro-(R) histatin 5 16mer as shown in FIG. 1, with L- or D-amino acids, respectively.

FIG. 3A shows the percent viability of *Candida albicans* SC5314 following exposure to the four histatin 5 peptide derivatives in the absence or presence of sodium azide ($NaN_3$). As controls, samples were exposed to sodium phosphate (NaPB) or sodium azide ($NaN_3$) alone;

sodium chloride (NaCl) was used to balance the overall salt concentration in each reaction. FIG. 3B shows the percent viability following exposure of *Candida albicans* SC5314 to the four histatin 5 peptide derivatives in the absence or presence of antimycin A (AMA). As controls, cells were incubated in NaPB+ethanol (EtOH) or NaPB+ethanol+ AMA. Ethanol was the solvent for AMA; hence, it was adjusted to the same concentration in all reactions. The W, WD, R and RD designates the wild-type (W) or retro-(R) histatin 5 16mer as shown in FIG. 1, with L- or D-amino acids, respectively.

FIG. 6A is a dose dependent assay. *Candida albicans* SC5314 cells were exposed to increasing concentrations of KM5 for 2 hours at 37° C. Cells were subsequently plated and grown on Sabouraud dextrose agar at 37° C. and colony counts were subsequently performed and compared to cells not exposed to the peptide. FIG. 6B shows the $LD_{50}$ calculated using a linear regression equation.

In FIG. 8A the killing activity of the histatin 5 16mer peptide (C-16) versus KM5 and KM6 are shown using 25 µM of each peptide incubated with *Candida albicans* SC5314 in 10 mM Sodium phosphate buffer for 2 hours at 37° C. The percentage of viable cells was calculated as (viable colonies in the presence of peptide/viable colonies without peptide)× 100. Data represents three independent experiments and the error bar represents the standard deviations. FIG. 8B shows a liposome leakage assay in which 1 µM of each peptide was incubated with artificial liposome and release of acridine orange was monitored for 24 minutes, then Triton X 100 was added to achieve 100% liposome lysis. Liposomes were incubated with sodium phosphate (NaPB) alone as a control.

DETAILED DESCRIPTION

Figure 3:
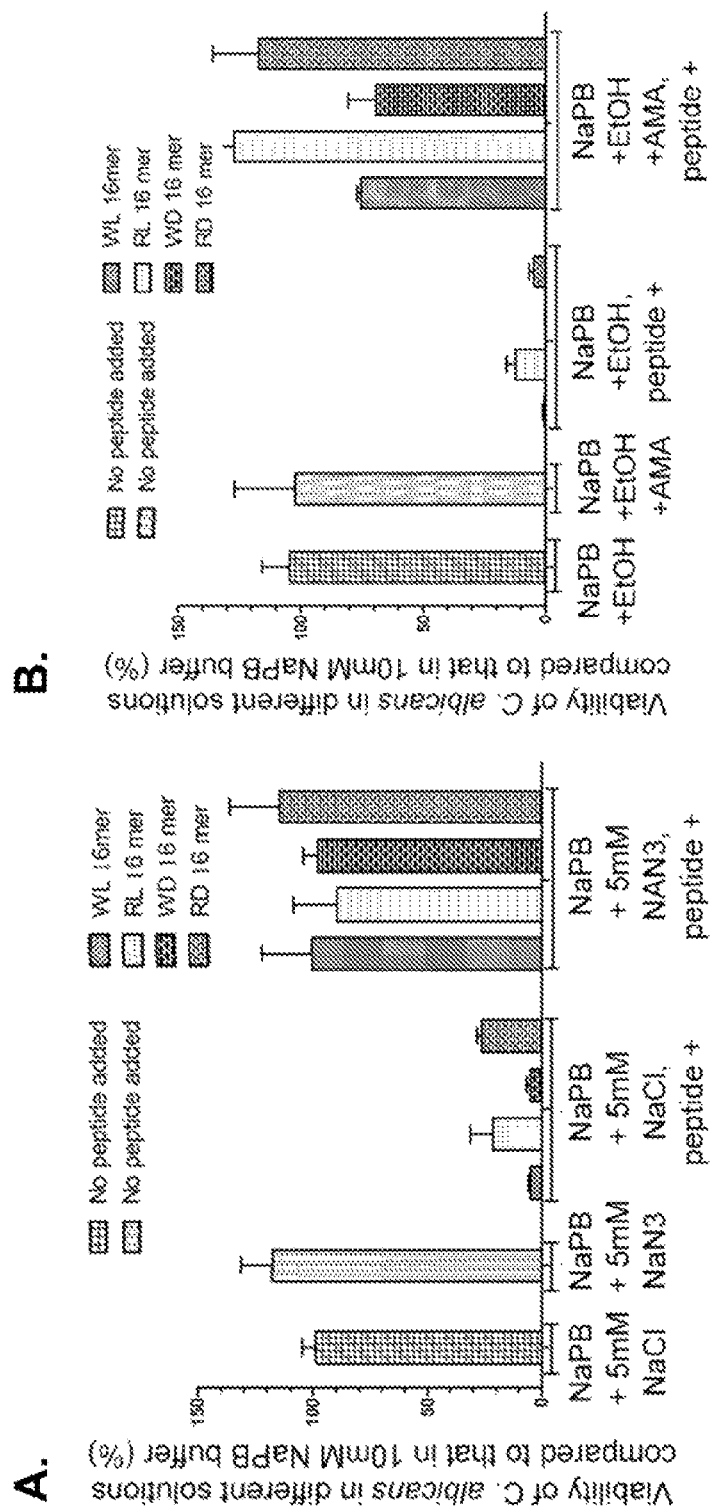
FIG. 3 is a set of graphs showing the fungal killing activity of histatin 5 16mer derivatives in the absence of respiratory activity.

A novel answer to the treatment of either mucosal or systemic fungal infections can be found in therapies that involve the use of small peptides that display fungicidal activity. Classically, the histatins are a family of naturally occurring peptides secreted into the oral cavity of primates, and some of the histatin peptides have antifungal activity. The predominant human histatins are 1, 3, and 5, with histatin 5 being the most potent antifungal.

The Examples provided herein define the minimal functional region of histatin 5 that displays significant antifungal activity. Once that region was defined, the derived information was used to generate peptide variants to enhance the fungicidal activity of the peptide. The goal was to generate the smallest peptide that would display the most potent fungicidal activity; thereby generating a potential antifungal therapeutic agent that would be economically feasible to produce. Through these studies, a five amino acid peptide is defined that maintains reasonable antifungal activity. Also provided are derivatives of the 5mer peptide. Some of these additional variants have significantly improved fungicidal activity. The activity of these peptides appears to have broad specificity among *Candida* species.

The invention features substantially pure peptides such as those provided in Table 1 below. The peptides provided herein contain a core region of 5 amino acids designated R1-R2-R3-R4-R5 where R1 is phenylalanine, tryptophan or tyrosine, R2 is lysine, R3 is arginine, R4 is lysine, and R5 is tyrosine, tryptophan or phenylalanine (SEQ ID NO: 1). The spatial position of the amino acids relative to each other is critical for antifungal activity with the relative positioning R1-R2-R3-R4-R5 (such as SEQ ID NO: 2); however, the reverse order R5-R4-R3-R2-R1 is equally effective with regards to its antifungal activity. In addition, the D-amino acid enantiomers were equally active in antifungal activity (SEQ ID NO: 10). The peptides used herein are synthetically made, but those of skill in the art will appreciate that such peptides could be made using other means such as via genetic engineering.

TABLE 1

Summary of the antifungal peptides described in this application.

| Peptide Name | Peptide Sequence[a,b,c] (SEQ ID NO:) |
|---|---|
| KM5 | F-K-R-K-Y (SEQ ID NO: 2) |
| KM6 | dF-dK-dR-dK-dY (SEQ ID NO: 10) |
| KM11 | C-F-K-R-K-Y (SEQ ID NO: 5) |
| KM12 | Y-K-R-K-F-C-----C-F-K-R-K-Y (SEQ ID NO: 17) |
| KM13 | C-W-K-R-K-W (SEQ ID NO: 18) |
| KM14 | W-K-R-K-W-C-----C-W-K-R-K-W (SEQ ID NO: 21) |
| KM15 | F-K-C-R-K-Y (SEQ ID NO: 22) |
| KM16 | F-K-C-R-K-Y (disulfide linked via Cys shown in bold) F-K-C-R-K-Y (SEQ ID NO: 22) |
| KM17 | C-F-K-R-K-Y-C (disulfide linked via Cys shown to form a circular peptide). (SEQ ID NO: 23) |
| KM23 | Y-K-R-K-F-F-K-R-K-Y (SEQ ID NO: 3) |
| KM29 | Y-K-R-K-F-K-R-K-Y (SEQ ID NO: 4) |

[a] The amino acid composition of each peptide is indicated by standard single letter designation.
[b] The inclusion of D-amino acids is indicated by a "d" presiding the amino acid single letter designation; otherwise they are assumed to be L-amino acids.
[c] Disulfide bonds are indicated by (-----) between cysteines.

The addition of an N-terminal cysteine (designated C) to the 5mer peptide (i.e. C-R1-R2-R3-R4-R5; such as shown in SEQ ID NO: 5, 16, 18, 20 and 23) does not negatively influence antifungal activity. A cysteine can also be added to the C-terminus of the peptide (such as in SEQ ID NO: 15 and 19). The cysteine may be used to generate a 5mer peptide dimer (i.e. R5-R4-R3-R2-R1-C-C-R1-R2-R3-R4-R5; such as SEQ ID NO: 17 or 21) that was shown to have substantially higher antifungal activity than the 5mer peptide. Repositioning of the cysteine residue (designated C) to the middle of the peptide (i.e. R1-R2-C-R3-3-R4-R5) to facilitate an alternative dimer structure maintained significant antifungal activity. In addition, cysteines (designated C) added to both the N- and C-termini (i.e. C-R1-R2-R3-R4-R5-C; such as in SEQ ID NO: 23) of the peptide to facilitate circularization also maintained significant antifungal activity.

In the final versions of the peptides, the cysteine residues have been removed and a 10mer peptide with the sequence R5-R4-R3-R2-R1-R1-R2-R3-R4-R5 (such as SEQ ID NO: 3 and 6) was generated. This peptide was as effective in fungal killing as the peptide dimerized via cysteines. More importantly, the possible concern related to the stability of the cysteine disulfide bonds was eliminated. Since the R1 amino acid was repeated at the center of the peptide, one additional 9 amino acid peptide with the sequence R5-R4-R3-R2-R1-R2-R3-R4-R5 (such as SEQ ID NO: 4 and 7) was generated. This peptide was found to be equivalent to the 10mer peptide in terms of antifungal activity.

Suitably the peptides used in the compositions provided herein are 5, 6, 7, 8, 9, 10, 11 or even 12 amino acids long. As described above more than one peptide (the same peptide, different peptides or inverted peptides) may be joined together via disulphide bonds between cysteine amino acid residues or via an amide linkage between the N- and C-terminus. A methionine can be added to the N-terminus of each of the peptides described herein or can be used to replace the N-terminal amino acid of the peptides provided herein. Peptides may also be circularized or dimerized using any other means known to those of skill in the art. Addition of a methionine to the N-terminus of the peptides provided herein can be used as a target to generate a circularized peptide using the method of Tam and Xu (Biopolymers (1998) Methionine ligation strategy in the biomimetic synthesis of parathyroid hormones 46: 319-329). For example, a methionine can be added to the N-terminus of a peptide such as SEQ ID NO: 3, 4, 6, or 7. Such an addition may aid in expression, modification or circularization of the peptide. Alternatively, a methionine can be used to replace the current N-terminal amino acid of one of the peptides provided herein, such as SEQ ID NO: 3, 4, 6 or 7. In addition, the C-terminal amino acid can be replaced with a threonine or a threonine could be added to the end of the peptides provided herein. The addition or substitution of a threonine at the C-terminus of the peptides may allow for increased expression in a recombinant model, easier modification of the peptides or increased activity of the peptides or to allow circularization of the peptides. The peptides may include one or more non-natural amino acids. Suitably the peptide is not the native peptide of SEQ ID NO: 8 or 24.

The peptides may have substituents bonded to either terminus of the peptide. For example, the peptide may have an acetyl or a carbamyl addition at the N-terminus, and/or an amide addition at the C-terminus. In addition, the peptides may be multimerized beyond a dimer, or circularized using standard chemistry to provide pharmacological stability for antifungal treatment. The multimers may contain more than one copy of one of the peptides disclosed herein or may contain inverse copies of a single peptide or more than one of the peptides disclosed herein. Those of skill in the art will appreciate that various additional modifications of the peptides provided herein may be made to increase the stability or half-life of the peptides in culture or in the subject after administration. For example fatty acids or other modifications may be added to the N-terminus including but not limited to formylation, myristoylation, or PEGylation. The peptide may be attached to a carrier protein to increase the stability of the peptide. The carrier protein-peptide may be a fusion protein and may be expressed as a recombinant protein using techniques available to those of skill in the art. The peptide bonds connecting the amino acids of the peptide may be altered or at least one peptide bond may be altered to make the peptides more resistant to degradation, for example a methyl group could be added. The amino acids could be replaced with functionally related non-natural amino acid that share similar side chains to the natural amino acid, such as replacement of the cysteine with homocysteine or α-methyl-cysteine. Alternatively peptoids based on the peptides provided herein could be generated. These and other peptidomimetics are expected to have similar antifungal activity to the peptides described herein.

The peptides described herein have potent antifungal properties. Several different *Candida* species have been shown to be susceptible to these peptides. The toxicity of the peptides has been examined both in vitro and in vivo (mice). The immunogenicity of the peptides has also been examined in mice and the peptides were only mildly immunogenic. Several peptides were also shown to not induce hemolysis of red blood cells.

The peptides may be used in methods for treating microbial infections, suitably fungal infections and potentially also bacterial infections. The methods include administering an effective amount of a peptide containing composition such as those described herein to a subject. The administration of the composition is effective to limit the spread of the microbial infection, inhibit the growth of the microbe or kill the microbe. Suitably, the microbe is a fungus or yeast and includes but is not limited to *Candida* spp., *Aspergillus* spp., *Histoplasma* spp., and *Cryptococcus* spp. In the Examples, the peptides are shown to have broad effectiveness against a variety of *Candida* species. Suitable subjects include humans, domesticated animals, and other non-human mammals. The compositions may be provided to subjects who are immunocompromised and may be effective in such subjects.

The peptide compositions may be used to make pharmaceutical compositions. Pharmaceutical compositions comprising the peptides described herein and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil -based or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified.

The peptide compositions provided herein may be administered in conjunction with other anti-microbials to treat a subject. The compositions may be administered in any order, at the same time or as part of a unitary composition. The peptide compositions provided herein may be administered with a second pharmaceutical such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

An effective amount or a therapeutically effective amount as used herein means the amount of a composition that, when administered to a subject for treating a disease or infection is sufficient to effect a treatment (as defined above). The therapeutically effective amount will vary depending on the composition, formulation of the composition, the disease and its severity and the age, weight, physical condition and responsiveness of the subject to be treated. The administration of the compositions may be effective to limit the spread of the microbial infection, inhibit the growth of the microbe or even kill the microbe.

The compositions described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or transmucosal absorption. Thus the compositions may be formulated as an ingestable, injectable, topical or suppository formulation. The compositions may also be delivered with in a liposomal or time-release vehicle. Administration of the compositions to a subject in accordance with the invention appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the compositions and formulations being administered, the route of administration, the disease to be treated or inhibited, the condition of the subject, and other relevant medical factors that may modify the activity of the composition or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions of the invention and of a known agent such as a polyene or azole, such as by means of an appropriate conventional pharmacological or prophylactic protocol.

The maximal dosage for a subject is the highest dosage that does not cause undesirable or intolerable side effects. As shown in the examples KM12 was well-tolerated in mice at dosages up to 10 mg/kg when injected via intravenous, intramuscular or intraperitoneal route. The number of variables in regard to an individual treatment regimen is large, and a considerable range of doses is expected. The route of administration will also impact the dosage requirements. It is anticipated that dosages of the composition will reduce symptoms of the infection at least 10%, 20%, 30%, 40%, 50%, 60%, 70%, 80%, 90% or 100% compared to pre-treatment symptoms or symptoms if left untreated. It is specifically contemplated that pharmaceutical preparations and compositions may palliate or alleviate symptoms of the disease without providing a cure, or, in some embodiments, may be used to cure the disease.

Suitable effective dosage amounts for administering the compositions may be determined by those of skill in the art, but typically range from about 1 microgram to about 100 milligrams per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one composition or more than one dose per week is administered, the effective dosage amounts correspond to the total amount administered. The composition can be administered as a single dose or as divided doses. For example, the composition may be administered two or more times separated by 4 hours, 6 hours, 8 hours, 12 hours, a day, two days, three days, four days, one week, two weeks, or by three or more weeks.

Methods of inhibiting microbial growth and in particular fungal growth are also provided herein. The methods include applying the composition to an object, such as a food item, surface or a liquid, including a cell culture medium, in an amount effective to prevent or limit microbial growth or contamination. The methods may also include contacting cells or cell culture fluid with the compositions provided herein. The method inhibits microbial or fungal growth in, on or with the cells or the cell culture fluid. The application or contact with the compositions provided herein may be effective to limit the spread of the microbe, inhibit continued growth of the microbe or even kill the microbe. Thus, the methods can be used in a preventative means or may be used to deal with and clean up an active microbial contamination.

The present disclosure is not limited to the specific details of construction, arrangement of components, or method steps set forth herein. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements. The terms "a", "an" and "the" may mean one or more than one unless specifically delineated. Recitation of ranges of values herein are merely intended to serve as a shorthand method of referring individually to each separate value falling within the range, unless otherwise indicated herein, and each separate value is incorporated into the specification as if it were individually recited herein.

The following examples are meant only to be illustrative and are not meant as limitations on the scope of the invention or of the appended claims. All references, included patents, patent publications and non-patent literature, cited herein are hereby incorporated by reference in their entirety. Any conflict between statements in references and those made herein should be resolved in favor of the statements contained herein.

EXAMPLES

Histatins are a family of structurally related histidine-rich peptides found in the oral cavity of humans and have a broad-range of antimicrobial activity. Of the histatin isoforms, histatin 5 shows the most potent antifungal activity (Helmerhorst, et al., J Biol Chem 274 (1999) 7286-7291). We synthesized a 16 amino acid derivative of histatin 5 known to be as active as the full length 24 amino acid histatin 5 (Raj et al., J Biol Chem 269 (1994) 9610-9619). In addition, the D amino acid enantiomer and the retro-histatin 5 and retro-enantio-histatin 5 using 1) amino acids were synthesized (FIG. 1). Following synthesis and purification by HIPLC, the four 16mer peptides were tested for antifungal activity against *Candida albicans* SC5314. Using a standard in vitro killing assay (Edgerton et al., J Biol Chem 273 (1998) 20438-20447) it was discovered that all four peptides maintained equivalent antifungal activity (FIG. 2).

Although all four peptides maintained equivalent antifungal activity, the question remained as to whether they were working via the same mechanism. To address this question, we took advantage of the fact that histatin 5 antifungal activity requires target cell respiratory activity (Gyurko et al., Antimicrobial Agents and Chemotherapy 44 (2000) 348-354). In other words, inhibiting cellular respiration rendered target fungal cells resistant to histatin 5 killing. Thus, we evaluated whether the four 16mer peptides synthesized in our laboratory required fungal cell respiration for killing activity. *Candida albicans* SC5314 was exposed to either sodium azide or antimycin A, two known respiratory inhibitors, and it was found that all four peptides lost antifungal activity in the presence of these inhibitors (FIG. 3), consistent with the presumption that all four 16mer derivatives were killing by the same mechanism.

Figure 4:
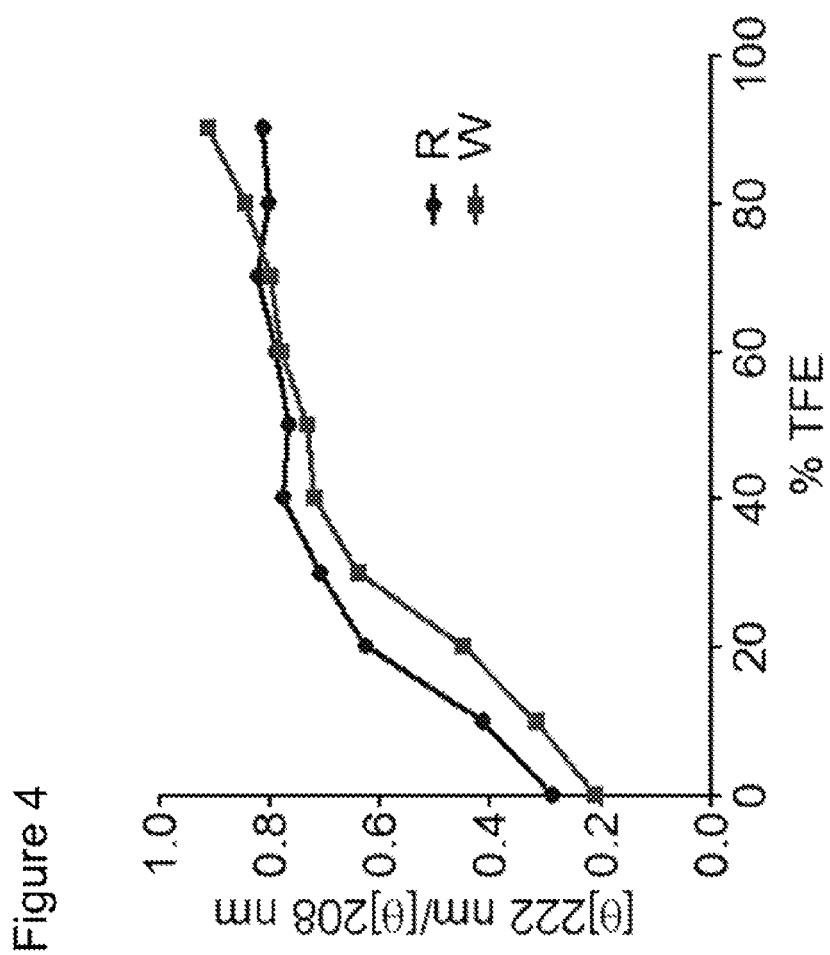
FIG. 4 is a graph showing that the secondary structure of the wild-type and retro-histatin 5 16mer peptides are similar. CD spectra were obtained on the wild-type histatin 5 16mer derivative (W) and the retro-histatin 5 derivative in the presence of increasing concentrations of trifluoroethanol (% TFE).

To evaluate whether the peptides adopt similar secondary structures, circular dichroism spectroscopy (CD) was performed on the wild-type and retro-histatin 5 16mer peptides in the presence of increasing concentrations of trifluoroethanol (TFE). We observed that both of these peptides showed similar propensities for alpha-helical formation in the presence of TFE (FIG. 4). The D-amino acid derivatives showed a similar profile since they would be the mirror image of the L-amino acid peptides.

Figure 5:
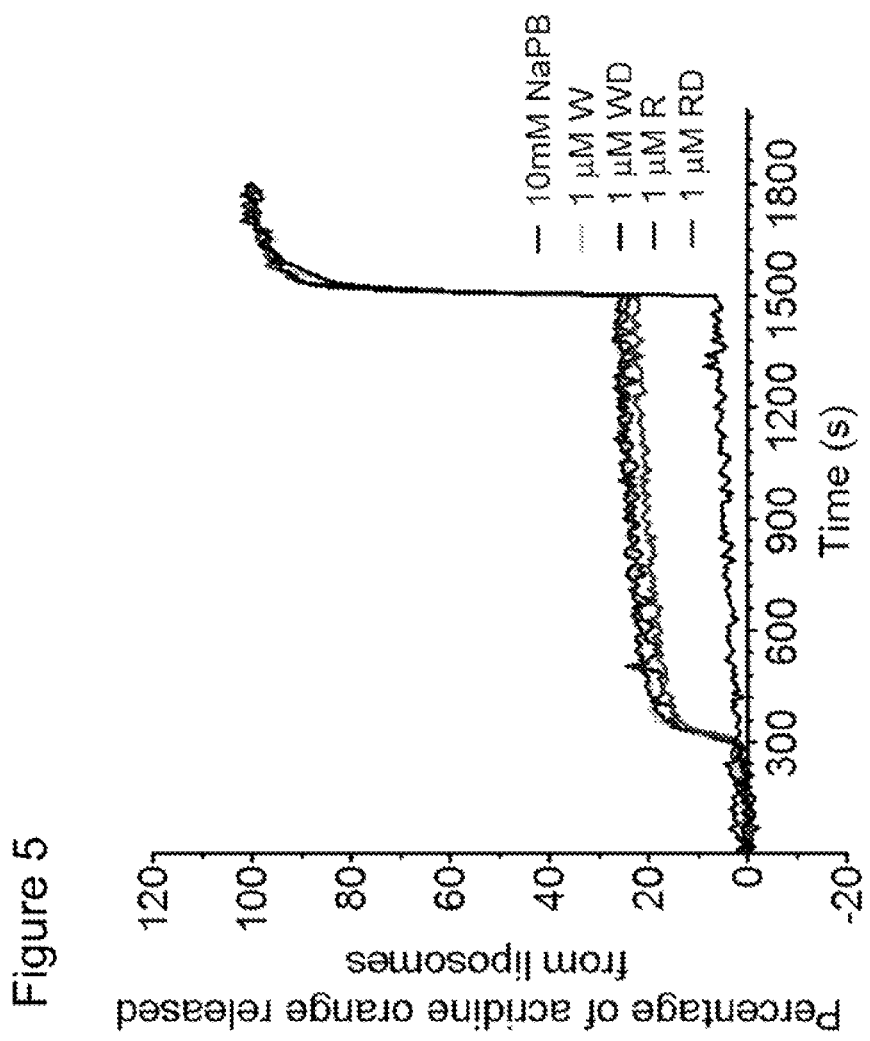
FIG. 5 is a graph showing the results of liposome fluorescence leakage assays. The four histatin 5 peptide derivatives at concentrations of 1 µM had comparable permeabilizing effects on artificial liposomes. The percentage of fluorescent leakage from liposomes in seconds (s) is compared to total leakage obtained with Triton X-100 at time 1800s. Maximal fluorescent intensities were in the range of 80,000-220,000 counts per second. As a control, liposomes were examined in sodium phosphate buffer (NaPB) only without peptide.

To quantify the ability of the four histatin 5 16mer peptide derivatives to lyse membranes, artificial liposomes were prepared with phospholipid and ergosterol concentrations similar to that of *Candida albicans*. The vesicles were loaded with acridine orange and a fluorescence release assay performed to compare the lysis potential of the four histatin 5 16mer derivatives (FIG. 5). It was determined that all four peptides showed comparable membrane lysis potential.

The preliminary studies led us to the hypothesis that there must be a region within histatin 5 that displays a quasi-dyad of symmetry such that the killing activity of the peptide is maintained whether it is the normal wild-type amino acid sequence or the retro sequence. Moreover, the enantiomeric form with D-amino acids would likely function identically. Given this hypothesis, we examined the sequence of histatin 5 and identified a small region of histatin 5 containing the sequence Y-K-R-K-F (SEQ ID NO: 24) (FIG. 1) that would fit the quasi-dyad of symmetry model with an arginine in the middle flanked by two lysines that are then flanked by two aromatic amino acids.

Figure 6:
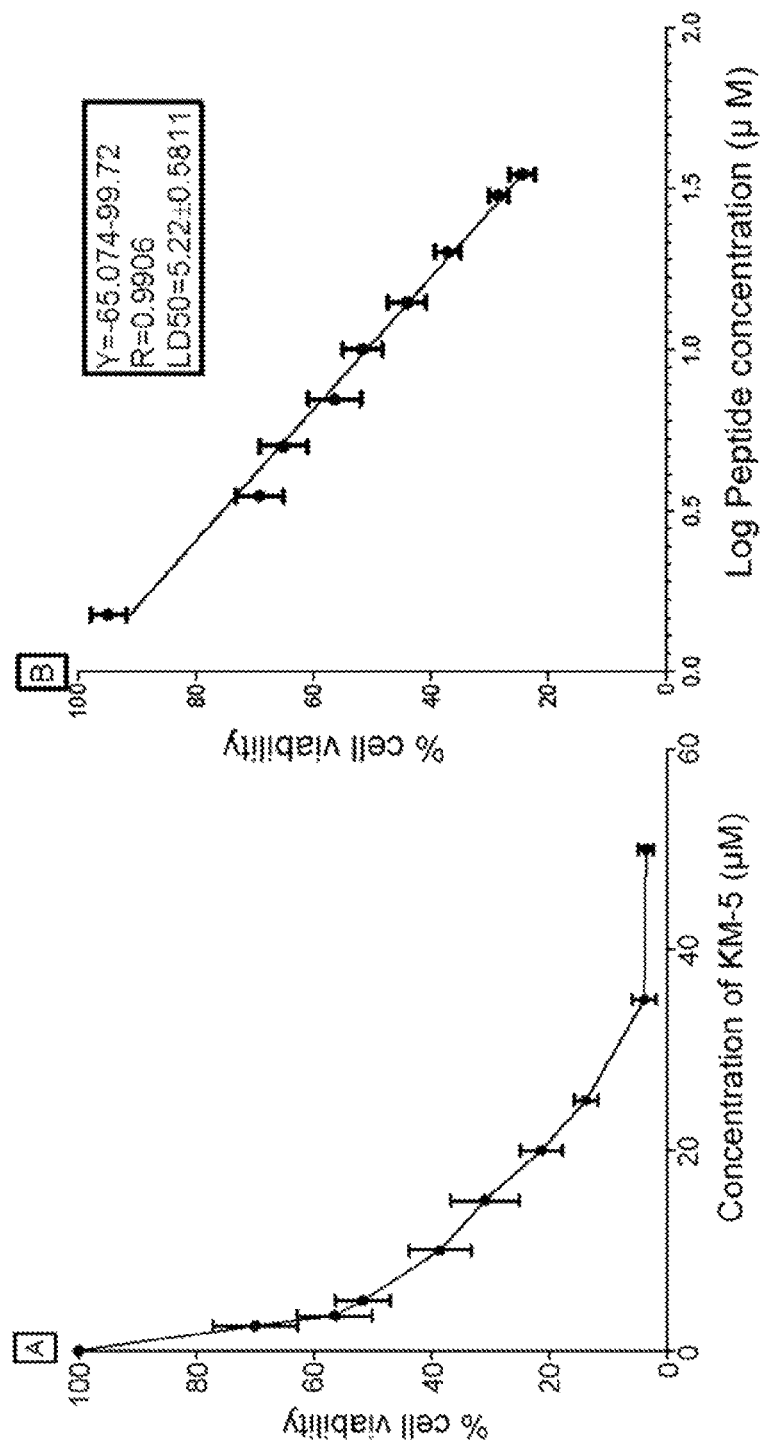
FIG. 6 is a set of graphs showing the determination of the $LD_{50}$ for KM-5.
Figure 7:
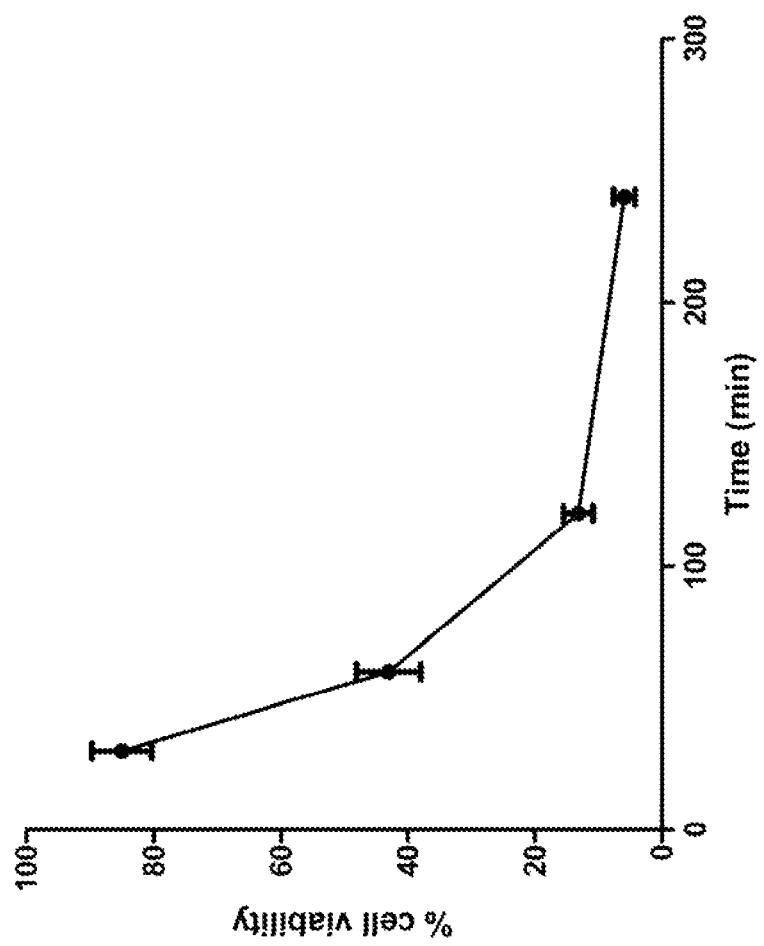
FIG. 7 is a graph showing the kinetics of antifungal activity with the KM-5 peptide. Time-dependent killing of *Candida albicans* SC5314 was evaluated by incubating cells with 10 µM peptide at 37° C. for various periods of time. The percentage of viable cells was calculated as (viable colonies in the presence of peptide/viable colonies without peptide)× 100. Data represents three independent experiments and the error bar represents the standard deviations.

To evaluate whether this sequence has antifungal activity, the F-K-R-K-Y (SEQ ID NO: 24) retro-5mer peptide was synthesized (designated KM5; SEQ ID NO: 2) and examined for antifungal activity in vitro. It was observed that KM5 displayed significant antifungal activity with an $LD_{50}$ of 5 µM (FIG. 6). Although KM5 was less potent as compared to the 16mer peptides (FIG. 2), it had significant antifungal activity and the smaller size was more conductive for large scale production. The kinetics of the antifungal activity of KM5 was also found to be time-dependent over a two hour period and the maximum killing activity was reached following two hours of incubation (FIG. 7).

Figure 8:
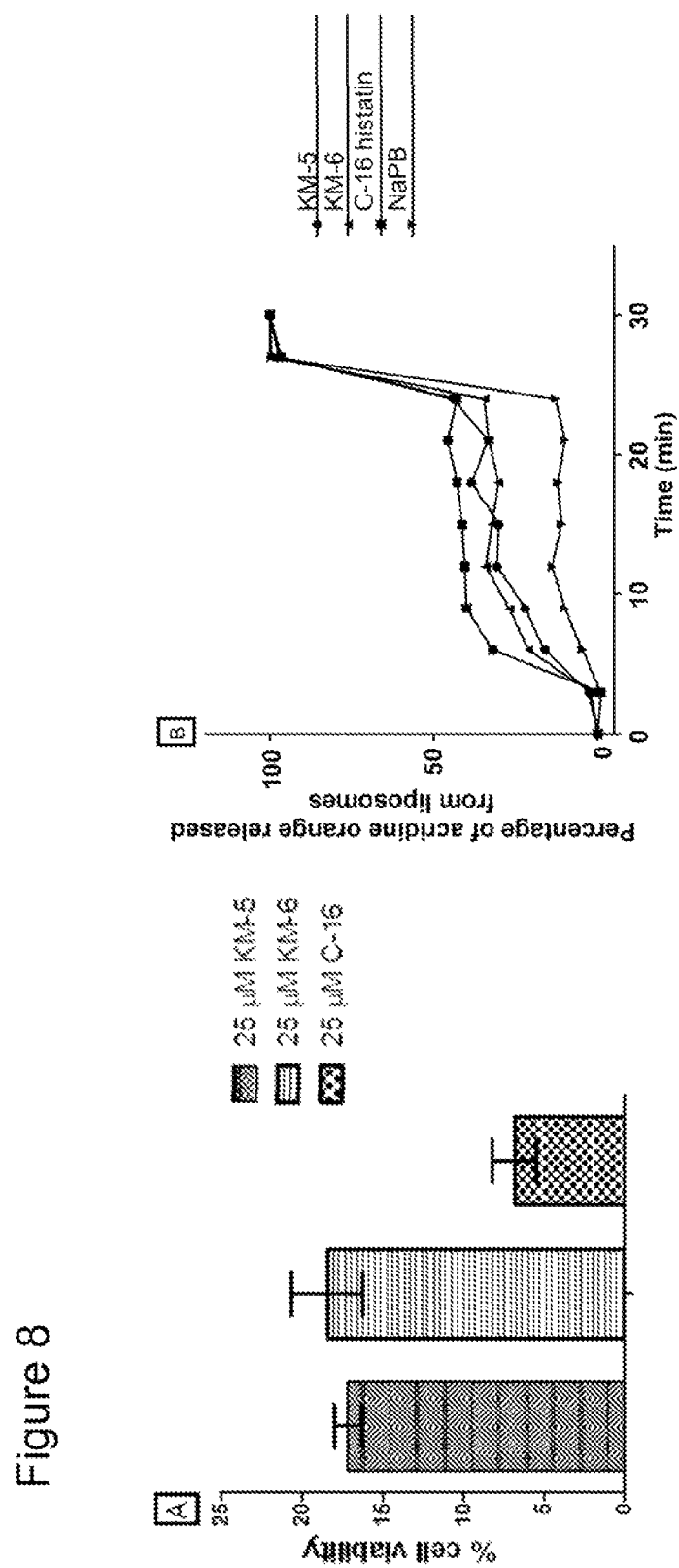
FIG. 8 is a set of graphs showing a comparison of the activity of KM-5, KM-6 and the histatin 5 16mer peptides.

We also synthesized the retro-5mer peptide with D-amino acids, KM6 (SEQ ID NO: 10), and found equivalent antifungal activity and the equivalent ability to permeabilize artificial liposomes in vitro (FIG. 8). This was particularly important because the D-amino acid peptides are likely to be resistant to proteolysis and more stable for use in the treatment of fungal infections in humans.

Thus, we focused on the further refinement of KM5 to obtain a more potent antifungal agent. To this end, we sought to determine the importance of the various residues within KM5 by synthesizing additional peptides that altered the amino acids at various positions as shown in Table 2. These peptides were synthesized and subsequently purified by HPLC. The peptides were then evaluated in a standard killing assay with *Candida albicans* SC5314. These data indicate that the arginine at position 3 is essential for killing activity (KM5 versus KM7 or KM8). Moreover, the tyrosine at position 5 shows greater fungicidal activity than phenylalanine at the fifth position (KM5 versus KM9). Overall, these data indicate sequence specificity in the fungicidial activity of KM5.

TABLE 2

Relative activity of the peptides at 25 µM

| Peptide name | Sequence (SEQ ID NO:) | Percent killing activity at 25 µM concentration |
|---|---|---|
| KM5 | FKRKY (L-amino acids; SEQ ID NO: 2) | 85% |
| KM6 | FKRKY (D-amino acids; SEQ ID NO: 10) | 90% |
| KM8 | FKSKY (SEQ ID NO: 12) | 0% |
| KM7 | FKPKY (SEQ ID NO: 11) | 3% |
| KM9 | FKRKF (SEQ ID NO: 13) | 70% |
| KM10 | KFRYK (SEQ ID NO: 14) | 55% |
| KM11 | CFKRKY (SEQ ID NO: 5) | 95% |

Figure 9:
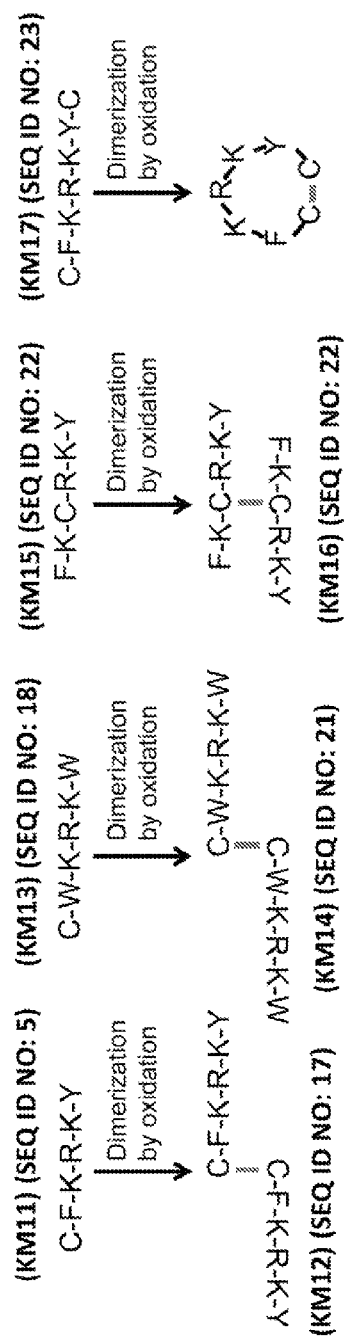
FIG. 9 is a schematic diagram of the different KM5 derivative peptides that were synthesized and subsequently dimerized via cysteine disulfide bonding. The disulfide bond is indicated with a thick line.
Figure 10:
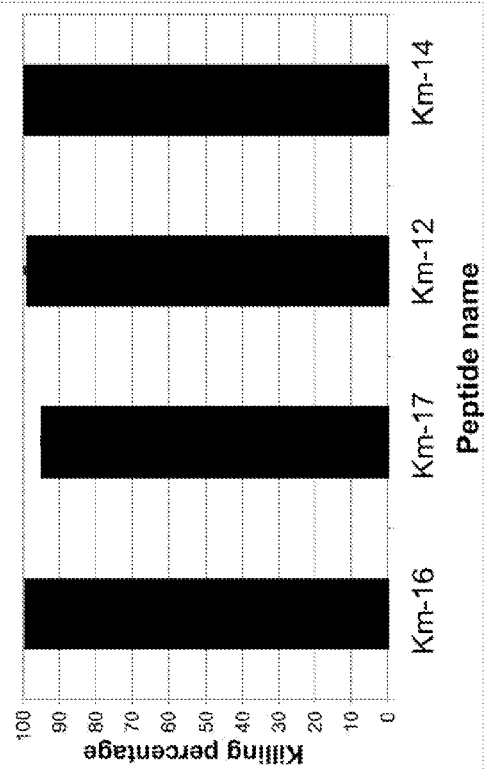
FIG. 10 is a graph showing a direct comparison of the relative fungicidal activity of KM12, KM14, KM16, and KM17 against *Candida albicans* SC5314. The peptides differ in structure as shown in FIG. 9, yet all four peptides kill >90% of *C. albicans* at 5 µM concentration.

The addition of a cysteine to the peptide did not alter its antifungal activity (KM11) (Table 2), yet permitted dimerization of the peptide via disulfide bonds. When the peptide (KM12) was dimerized, we observed a dramatic enhancement in antifungal activity ($LD_{50}$=172 nM). In an effort to further exploit potential peptide-membrane interactions, we modified both the tyrosine and phenylalanine residues to tryptophan (KM14); however, this resulted in a slight loss of antifungal activity (LDR=528 nM). Nevertheless, KM14 remained a viable compound for animal testing. To evaluate whether the position of the cysteine at the N- or C-terminus was critical for activity, it was moved to the center of the peptide (KM16) (FIG. 9). In addition, we synthesized a 7mer peptide with cysteines at both the N- and C-termini and circularized the peptide via disulfide bonding, KM17 (FIG. 9). The dimerized KM5 peptides designated KM16 and KM17 have very promising antifungal activity compatible with that of KM12 and KM14, and we are continuing to evaluate their toxicity to mammalian cells and fungicidal activity.

As we evaluated these peptides for protein binding activity using bovine calf serum, it was discovered that the disulfide bond in KM12 was readily reduced generating two 6mer peptides with significantly less antifungal activity. To alleviate that difficulty, two additional peptides were synthesized, KM23 and KM29. The KM23 peptide was identical in sequence to KM12 except the cysteine residues were removed resulting in a peptide with the sequence Y-K-R-K-F-F-K-R-K-Y (SEQ ID NO: 3). Since there were two phenylalanines at the center of this symmetrical peptide another peptide, designated KM29 was synthesized to yield the symmetric peptide Y-K-R-K-F-K-R-K-Y (SEQ ID NO: 4) with one phenylalanine at the center. Both of these peptides were evaluated for antifungal activity against *Candida albicans* SC5314 as well and found to have an $LD_{50}$ of 62.5 nM in killing assays.

To further compare the activity of KM12, KM23 and KM29 for antifungal activity, a minimum inhibitory concentration (MIC) assay was performed with several different species of *Candida*. Table 3 indicates that all three peptides show similar profiles of killing activity with (*Candida* species including *C. albicans, C. kefyr, C. glabrata, C. krusei, C. lucitaniae,* and *C. tropicalis*. Each of the *Candida* species were clinical isolates obtained from the ATCC. We are continuing to evaluate the sensitivity of other *Candida* species to the peptides including *C. dubliniensis, C. parapsilosis* and other independent isolates of *C. albicans*. At the preliminary stage, we have observed a broad spectrum of activity against most *Candida* species with *C. glabrala* showing the most resistance to KM12, KM23, and KM29.

TABLE 3

MIC assays for KM12 (SEQ ID NO: 17), KM23 (SEQ ID NO: 3), and KM29 (SEQ ID NO: 4) [a]

| *Candida* species | KM12 | KM23 | KM29 |
|---|---|---|---|
| *Candida albicans* SC5314 | 5.5-11 | 4.7 | 4.2-8.4 |
| *Candida kefyr* ATCC4135 | 2.6-5.5 | 1.2-4.7 | 2.1-4.3 |
| *Candida glabrata* ATCC90030 | 88 | 75.4 | 67.5 |
| *Candida krusel* ATCC6258 | 5.5-11.0 | 4.7 | 4.2 |
| *Candida lucitaniae* ATCC200951 | 1.4-2.8 | 2.4 | 2.1-4.2 |
| *Candida tropicalis* ATCC750 | 2.8-5.5 | 2.4-4.7 | 2.1-4.2 |

[a] Values are presented in µg/ml of each peptide. Each MIC assay represents three independent experiments with the range indicated for each. MIC assays were performed in 0.125X RPMI medium.

Figure 11:
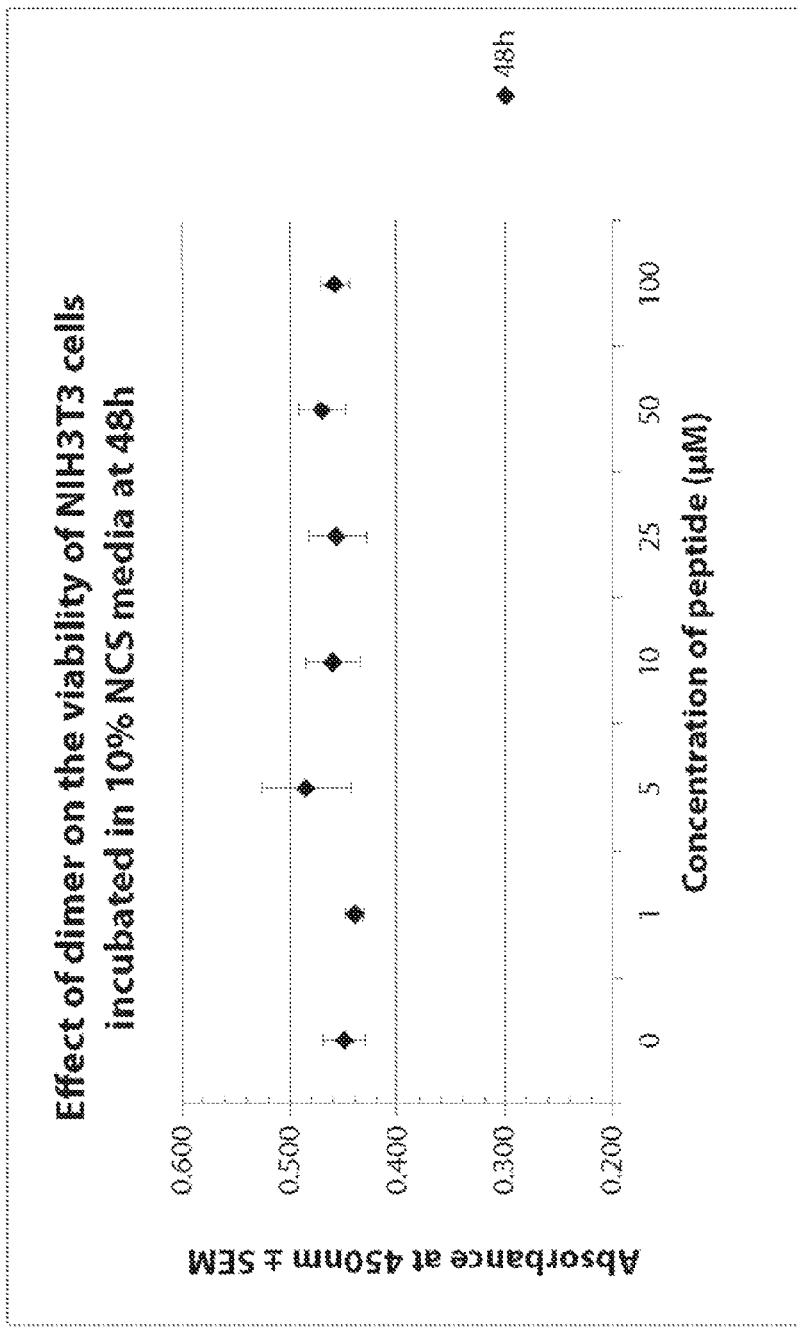
FIG. 11 is a graph showing the toxicity of the KM12 peptide to NIH3T3 mammalian cells. Cells were incubated in culture with the KM12 peptide at the concentrations indicated. After 48 hours, the WST1 cell proliferation assay was performed to evaluate cell viability. No loss in viability was noted. The assay was performed three times independently and the average is shown with error bars indicating the standard error.

To evaluate whether these peptides cause toxicity to mammalian cells, we examined toxicity using cell proliferation assays. We observed no significant mammalian cell toxicity after 48 hours of incubation in the presence of KM12 at concentrations as high as 100 µM (FIG. 11). In addition, mammalian cells were also examined by FACS analysis with a propidium iodide uptake assay to determine whether the peptide caused permeabilization of the mammalian cell plasma membrane. No significant membrane permeabilization was observed.

Figure 12:
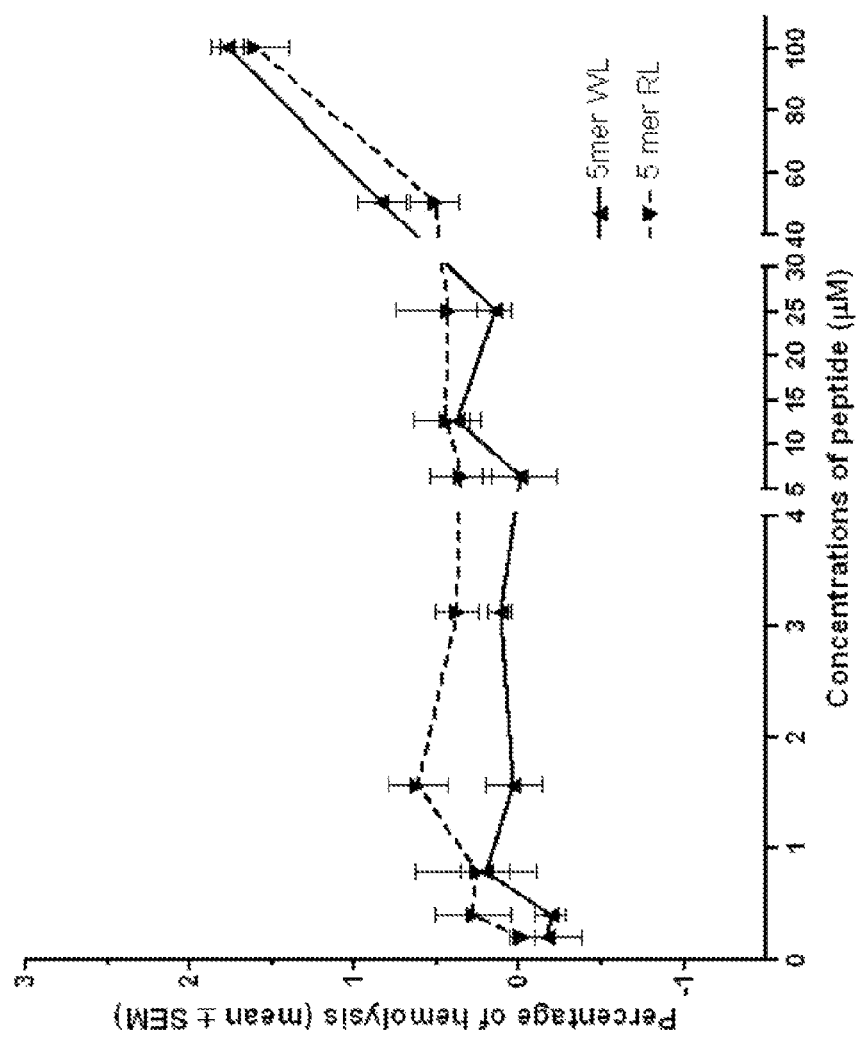
FIG. 12 is a graph showing hemolysis of red blood cells by KM5. Sheep red blood cells were incubated with the indicated concentrations of KM5 or retro KM5 (reverse sequence order) for 1 hour at 37° C. The percentage of hemolysis was subsequently determined by the absorbance at 405 nm as outlined in the Methods section. The assay was performed three times independently and the average is show with the error bars indicating the standard error.
Figure 13:
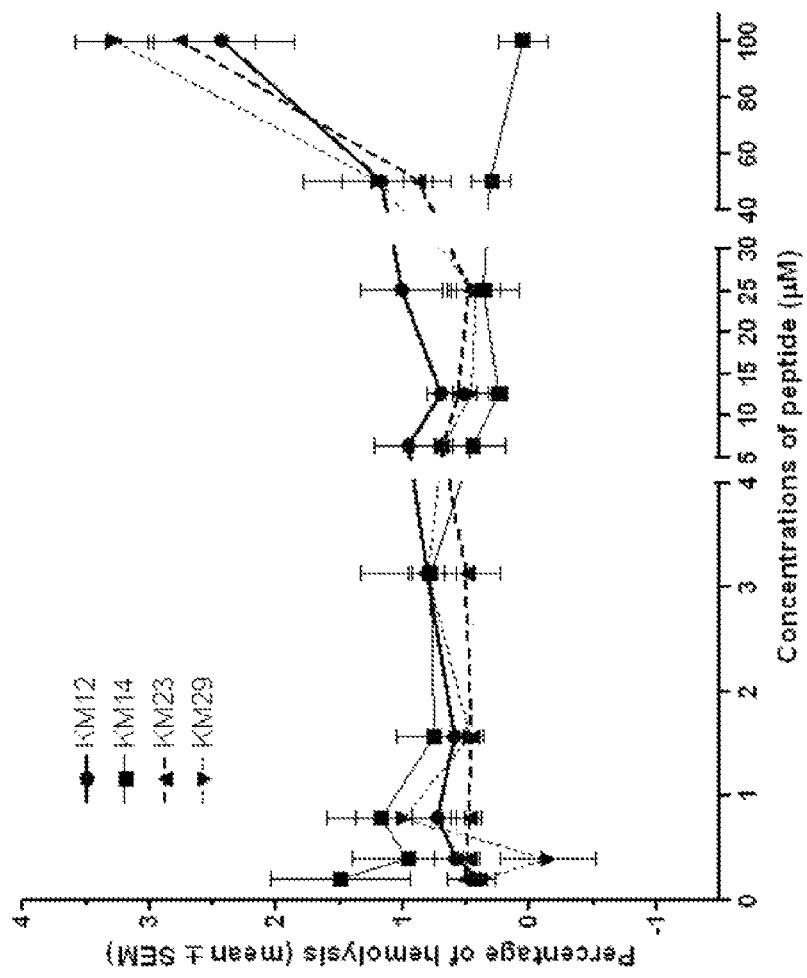
FIG. 13 is a graph showing hemolysis of red blood cells by KM12, KM14, KM23, and KM29. Sheep red blood cells were incubated with the indicated concentrations of the peptides for 1 hour at 37° C. The percentage of hemolysis was subsequently determined by the absorbance at 405 nm as outlined in the Methods section. The assay was performed three times independently and the average is show with the error bars indicating the standard error.

To evaluate whether the various peptides have hemolytic activity, we examined the hemolysis of sheep red blood cells in the presence of KM5 and retro KM5 (FIG. 12) and the dimer peptides KM12, KM14, KM23, and KM29 (FIG. 13). None of the aforementioned peptides displayed significant hemolysis activity (3% or less) at peptide concentrations up to 100 µM. Thus, the KM peptides did not result in significant red blood cell hemolysis in vitro.

To evaluate acute toxicity in animals, CD1 outbred mice were injected via tail vein with either KM12 or KM14 using a standard up-down concentration protocol and observed for any symptoms consistent with the toxicity of the peptides (Table 4). Mice were initially injected with KM12 or KM14 at a concentration of 8 mg/kg. KM12 peptide showed no toxicity at this concentration with five different animals; however, KM14 caused immediate death with two mice and the acute toxicity evaluation of this peptide was terminated. After examining a limited number of peptide concentrations and solvent formulations it was determined that KM12 at 10 mg/kg administered in 5% glucose either intravenously, intramuscularly or intraperitoneally caused no major toxicity. Thus the KM12 peptide was deemed safe for animals at concentrations up to 10 mg/kg and the use of 5% glucose versus phosphate-buffered saline was deemed safer for administration to the animals. We will continue to evaluate acute toxicity with other KM peptides (i.e. KM23 and KM29) that show excellent promise as antifungal compounds. In addition, we plan to evaluate these peptides for treatment of superficial mucosal infections with Candida species.

(both were contained 0.1% TFA). The purity of each peptide was evaluated by mass spectroscopy. The peptides concentrations were determined by the extinction coefficient.

Killing assays. The fungicidal activity of the peptides toward *Candida albicans* was examined by microdilution

TABLE 4

Acute toxicity testing of KM12 (SEQ ID NO: 17) and KM14 (SEQ ID NO: 21) in CD1 mice

| PEPTIDE USED[a] | DOSAGE and Route of Administration[b] | SIGNS OBSERVED ON TESTED ANIMALS |
|---|---|---|
| KM12 IN PBS (n = 5) | 8 mg/kg, IV | None |
| KM12 IN PBS (n = 6) | 16 mg/kg, IV | Reduced motor activity (n = 4), protruding eyeballs accompanied by convulsion (n = 3), death (n = 1) |
| KM12 IN PBS (n = 5) | 12 mg/kg, IV | Labored breathing (n = 4), reduced motor activity (n = 4), protruding eyeball (n = 1), redness in ear skin (n = 1) |
| KM12 IN PBS (n = 5) | 10 mg/kg, IV | None |
| KM12 in 5% Glucose (n = 2) | 16 mg/kg, IV | Convulsion, no death |
| KM12 in 5% glucose (n = 15) | 10 mg/kg, IV, IM, IP | None |
| KM14 IN PBS (n = 2) | 8 mg/kg, IV | Death |

[a]peptides were dissolved in either phosphate-buffered saline or a solution containing only 5% glucose. n indicated the number of mice used for each study.
[b]dosage in mg of peptide per kg mouse weight. Route of adminisration includes intravenous (IV), intramuscular (IM), or intraperitoneal (IP).

Small peptides have the potential to induce an immune response when used for therapeutic purposes. To examine this possibility, mice were injected once per month for four months with 10 mg/kg of the KM12 peptide either by intravenous, intramuscular, or intraperitoneal route. After the fifth month, the mice were euthanized and the serum collected and tested by dot blot analysis for antibodies directed against the KM12 peptide. For each route of injection, five CD1 mice were used. It was observed that 1/5 mice showed a moderate immune response to KM12 following intravenous injection, 1/5 mice displayed a weak immune response following intramuscular injection, and 0/5 mice displayed an immune response after intraperitoneal injection. These data suggest that KM12 is weakly immunogenic; however, the smaller peptides, KM23 and KM29, have not been evaluated. It is plausible that the smaller size of those peptides may not elicit an immune response, yet be effect as antifungals. Such studies are currently underway on KM23 and KM29.

Methods:

Peptide Synthesis. N-Fmoc protected amino acids and Rink resin was purchased from NovaBiochem (San Diego, Calif.) and Advanced Chemtech (Louisville, Ky.). All KM peptides were synthesized with an acetylated N-terminus and amidated C-terminus. The peptides were synthesized on a Model 433A solid-phase peptide synthesizer (Applied Biosystems; Foster City, Calif.) using Rink resin and Fmoc-protected amino acids (NovaBiochem). After synthesis, the peptides were deprotected and cleaved from the resin using a high TFA (trifluroacetic acid) cleavage cocktail consisting of 85% TFA, 5% dH2O, 5% triisopropylsilan, and 5% Phenol. The resin was subsequently mixed in the cocktail solution at room temperature for 3 hours, after which peptide precipitated into 50 ml's 1:1 v/v methyl-t-butyl ether/hexane per ml of cleavage cocktail. Next, the peptides were dissolved in 1:1 v/v acetonitrile/ddH2O and recovered by lypholyzation under high vacuum. Crude peptides were purified on Prp-3 reverse phase column (7 by 305 mm; Bio-Rad, Hercules, USA) on a Hitachi L7100 HPLC instrument using a linear gradient of 0-30% acetonitrile and water plate assay as described previously (13). Briefly, from a fresh overnight cultured plate, a single colony was inoculated and diluted in 1 ml of 10 mM sodium phosphate buffer at pH 7.4. Once cell counts had been confirmed by using a hemocytometer, the cells diluted within the same buffer at $1.8 \times 10^5$ cells/mil. Cell suspensions of 20 μl were mixed with 20 μl of peptide, which were dissolved in 10 mM sodium phosphate buffer at pH 7.4, and then incubated for 2 hours at 37° C. with shaking at speeds of 550 rpm. The reactions were stopped by the addition of 360 μl yeast nitrogen base (YNB) and then 40 μl of cell suspension was spread onto plates and incubated for 24 hours at 37° C. Sabouraud dextrose agar plates were used for *C. albicans* killing assay. The number of colony-forming units (CFUs) was counted and each assay was repeated in triplicate. Loss of viability was calculated as [1-(colonies from suspension with peptide/colonies from suspension with no peptide)]×100. For the respiratory activity experiments, *Candida albicans* was grown in the presence of sodium azide or antimycin A (Sigma Aldrich) before the killing assay was performed.

Circular Dichroism Spectroscopy. CD measurements for the peptides were acquired on a Jasco-710 spectropolarimeter. The readings were done using a quartz cell of 0.1 cm path length at 25° C. Peptides was measured in increasing concentrations of trifluoroethanol (IFE) (vol/vol). The spectra were recorded between 190 nm and 250 nm every 0.2 nm, with a 1.0 nm bandwidth and a scan speed of 20 nm/min. The background was subtracted from all spectra and smoothened using the Fourier filters. The CD spectra are reported as the mean residue molar ellipticity ([θ]) in $degrees.cm^2.dmol^{-1}$.

Fluorescence Leakage Assay: Reagents included: 1,2-dipalmitoyl-sn-glycero-3-phosphocholine (DPPC, catalog #850355), 1,2-dipalmitoyl-sn-glycero-3-phosphoethanolamine (DPPE, catalog #850705), Soy PI (catalog #840044) and 1 μm polycarbonate membranes (catalog #610010) purchased from Avanti Polar Lipids. Ergosterol was purchased from Avanti Polar Lipids. PD-10 desalting columns (catalog #17-0851-01) were purchased from GE Health care Life Sciences. Ergosterol-containing liposomes were prepared from phospholipids and ergosterol dissolved in an organic solvent containing chloroform:methanol:water at a volume ratio of 65:35:8. Lipid mixtures were prepared at a concentration of 12 mg per 1 ml of organic solvent and had a weight ratio of DPPC:DPPE:SoyPI:ergosterol of 5:4:1:2. This relative ratio mimics *C. albicans* yeast biomembranes (14, 15). Lipid mixtures were thoroughly mixed, dried under a nitrogen stream for 20 to 30 minutes, and then evaporated in a vacumn evaporator overnight. Lipid cakes were hydrated with 1 ml of 110 mM ammonium sulfate for a period of 1 hour at 72° C. in a water bath with vigorous shaking. Lipid suspensions were subjected to three freeze-thaw cycles and extruded through stacked 1 μm polycarbonate membranes for at least 17 cycles to yield large unilamellar vesicles. The extrusion was performed at 72-75° C. using a thermo-controller. Buffer exchange was done after extrusion by gel filtration as per protocol provided with PD10 desalting columns (GE Health Care Life Sciences). The buffer exchange step replaced the external liposomal buffer of 110 mM amonium sulfate with 150 mM sodium chloride. The size distribution of unilamellar vesicles (liposomes) in the final lipid suspensions was evaluated with a Zeta Potential Analyzer Utilizing Phase Analysis Light Scattering Machine (Zetapals, Brookhaven Instruments Corp.). Liposomes in 150 mM sodium chloride were stored at 4° C. until used. For fluorescent leakage assays, liposomes were loaded with 10 μM acridine orange in 10 mM sodium phosphate buffer (pH 7.4) supplemented with 5% glucose. A 60 μl of liposome suspension was added into 1940 μl of 10 μM acridine orange in 10 mM sodium phosphate buffer/5% glucose and kept at room temperature in the dark for 4 hours. External acridine orange was removed by gel filtration with the use of PD10 desalting columns. During this gel filtration step, the external-liposomal solution of 150 mM sodium chloride was replaced with 10 mM sodium phosphate buffer pH 7.4/5% glucose. Acridine orange-loaded liposomes in 10 mM sodium phosphate buffer/5% glucose were tested with the four 16-mer peptides in four-sided polystyrene cuvettes (Sarstedt). The fluorescent intensity of the 2 ml samples was monitored by Fluoromax 4P instrument (Horiba Scientific). More specifically, 120 μl of peptides were added into 1880 μl of liposome suspensions at 300 seconds to a final peptide concentration of 20 μM and 10% Triton X-100 was added at 1500 seconds to a final Triton X-100 concentration of 0.1%. For control samples. 120 μl of 10 mM sodium phosphate buffer was added into liposome suspensions instead of the peptides. The fluorescent intensity of the whole samples was monitored during a 30 minute period (excitation 490 nm, emission 525 nm) and plotted as percentage of acridine orange release compared to the total release obtained with Triton X 100. The formula used to calculate percentage of release is as followed:

$$\text{Percentage of fluorescence release} = 100\% \times \frac{Ft - Fo}{Ftotal - Fo}$$

Ft: fluorescent intensity at time t; Fo: fluorescent intensity at time 0
Ftotal: fluorescent intensity obtained with triton X-100 at time 1800s Minimum Inhibitory Concentration Assays: MIC assays were used to evaluate the minimum concentration of each antifungal peptide that would lead to 100% inhibition of growth. In the MIC assay, the colorimetric indicator, resazurin, is used to evaluate cell growth. Resazurin turns pink after reduction by living cells, indicating active cell growth. The unchanged blue color indicated no active cell growth. Colorimetric MIC end-points are interpreted as the lowest drug concentration that remained blue. The lowest dilution that changed from blue to slightly purple is indicative of significant cell growth inhibition; whereas a pink color indicates no growth inhibition. Each individual *Candida* species was assayed a minimum of three times and the results represent the range of MIC values obtained. The MIC assay was performed as described by the National Committee for Clinical Laboratory Standards M27-A, except we include resazurin as an indicator dye rather than visual inspection and the RPMI1690 tissue culture medium was used at 0.125× concentration for our assays.

Antifungal peptide toxicity to mammalian cells in vitro. To evaluate the toxicity of the peptide to mammalian cells, NIH3T3 cells were grown in cell culture using Dulbecco's modified essential medium (DMEM) containing 10% newborn calf serum (NCS). The KM12 peptide was added at various concentrations and incubated with the cells for up to 48 hrs. WST-1 cell viability assay (Roche) was performed as described by the manufacturer after 48 hrs. to evaluate the loss of cell viability.

Hemolysis Assays. Red blood cell hemolysis assays were performed using sheep red blood cells in a 96-well microtiter plate format. The peptide dissolved in phosphate -buffered saline (pH 7.2) was prepared by two-fold serial dilutions in a 96-well titer plate in a final volume of 100 μl. The maximum concentration of peptide was 100 μM. Positive control used Triton X-100 at a final concentration of 1% to achieve maximum red blood cell lysis. The negative control contained only phosphate-buffered saline. For the assay, 100 μl of 1% sheep red blood cells in phosphate-buffered saline were added to wells prepared as described above and the cells were incubated at 37° C. for one hr with shaking at 170 rpm. The plates were subsequently centrifuged at 1000×g for 5 min. and 100 μl of the supernatant per well was collected for the measurement of absorbance at 405 nm by a microtiter plate reader (Bio-Tek Instruments, Inc. EL808). The percentage of hemolysis was calculated by the following equation:

$$\text{Percentage of hemolysis} = 100\% \times \frac{\text{Abs(sample)} - \text{Abs(negative control)}}{\text{Abs(positive control)} - \text{Abs(negative control)}}$$

Where:
Abs (sample) is the absorbance of supernatant obtained from the samples treated with peptides
Abs (negative control) is the absorbance of supernatant obtained from the samples treated with phosphate buffered saline
Abs (positive control) is the absorbance of supernatant obtained from the samples treated with 1% Triton X-100.

Animal Studies: For the animal studies, CD-1 mice of 8-25 grams were injected with the antifungal peptides dissolved in either phosphate-buffered saline or 5% glucose. Peptide concentrations used for the injection of mice were chosen using a standard up-down protocol starting at 8 mg/kg. Peptides were injected into mice intravenously, intramuscularly, or intraperitoneally as indicated. The mice were closely monitored lbr signs of distress after injection. After two hours of continuous monitoring, the mice were evaluated daily for two weeks and necropsies performed after two weeks. For evaluating the immunogenicity of the peptides, mice were injected with peptides at a concentration of 10 mg/kg in 5% glucose. The routes of injection were intravenous, intramuscular, or intraperitoneal. Five mice were injected with the peptide per route of injection. The mice were injected with the same dose of peptide once per month for four months. The mice were monitored for signs of distress after each injection. At the end of the fifth month, the mice were euthanized by an overdose of anesthesia and the serum was collected from each mouse individually as assay for activity against the peptide using dot blots.

We claim:

1. An antifungal composition comprising a peptide of SEQ ID NO: 3 (Y-K-R-K-F-F-K-R-K-Y) or SEQ ID NO:4 (Y-K-R-K-F-K-R-K-Y).

2. The composition of claim 1, wherein the amino acids are D amino acids.

3. The composition of claim 1, further comprising a cysteine in the peptide, wherein the cysteine is positioned at the N-terminus, the C-terminus or in both of these positions.

4. The composition of claim 1, wherein the peptide is circularized.

5. The composition of claim 1, wherein the peptide is no more than 12 amino acids long.

6. The composition of claim 1, wherein the peptide is not circularized or is N-terminally modified.

7. A pharmaceutical composition comprising the composition of claim 1.

8. A method of treating a microbial infection in a subject, comprising administering an effective amount of the composition of claim 1 to a subject in need thereof.

9. The method of claim 8, wherein the microbial infection is a fungal infection.

10. The method of claim 9, wherein the fungal infection is a *Candida, Aspergillus, Histoplasma,* or *Cryptococcus* infection.

11. The method of claim 8, wherein the subject is human or a non-human mammal.

12. The method of claim 8, wherein the composition is administered via a route selected from oral, topical, intranasal, intraperitoneal, parenteral, intravenous, intramuscular, subcutaneous, intrathecal, transcutaneous, nasopharyngeal, or via transmucosal absorption.

13. A method of inhibiting microbial growth, comprising applying the composition of claim 1 to an object to inhibit microbial growth, wherein the object is selected from the group consisting of a food, a surface or a liquid.

14. The method of claim 13, wherein the microbial growth is growth of a fungus selected from the group consisting of a *Candida, Aspergillus, Histoplasma,* and *Cryptococcus* fungus.

15. A method of inhibiting microbial growth in, on or with a cell, comprising contacting a cell with the composition of claim 1, wherein microbial growth in, on or with the cell is inhibited.

* * * * *

UNITED STATES PATENT AND TRADEMARK OFFICE
CERTIFICATE OF CORRECTION

PATENT NO. : 9,556,226 B2
APPLICATION NO. : 14/777321
DATED : January 31, 2017
INVENTOR(S) : Suresh Kumar Thallapuranam et al.

It is certified that error appears in the above-identified patent and that said Letters Patent is hereby corrected as shown below:

In the Specification

Column 1 Line 16 should read:
This invention was made with government support under Grant Numbers RR015569, RR031154 and GM103450 awarded by the National Institutes of Health. The government has certain rights in this invention.

Signed and Sealed this
Thirty-first Day of December, 2019

Andrei Iancu
*Director of the United States Patent and Trademark Office*

SEQUENCE LISTING

```
<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be Trp, Phe, or Tyr
<220> FEATURE:
<221> NAME/KEY: misc_feature
<222> LOCATION: (5)..(5)
<223> OTHER INFORMATION: Xaa can be Trp, Phe, or Tyr

<400> SEQUENCE: 1

Xaa Lys Arg Lys Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide: KM5

<400> SEQUENCE: 2

Phe Lys Arg Lys Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide: KM23

<400> SEQUENCE: 3

Tyr Lys Arg Lys Phe Phe Lys Arg Lys Tyr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide: KM29

<400> SEQUENCE: 4

Tyr Lys Arg Lys Phe Lys Arg Lys Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide: KM11

<400> SEQUENCE: 5
```

```
Cys Phe Lys Arg Lys Tyr
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be Phe or Tyr
<220> FEATURE:
<221> NAME/KEY: misc_feature
<222> LOCATION: (5)..(6)
<223> OTHER INFORMATION: Xaa can be Phe or Tyr
<220> FEATURE:
<221> NAME/KEY: misc_feature
<222> LOCATION: (10)..(10)
<223> OTHER INFORMATION: Xaa can be Phe or Tyr

<400> SEQUENCE: 6

Xaa Lys Arg Lys Xaa Xaa Lys Arg Lys Xaa
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa can be Phe or Tyr
<220> FEATURE:
<221> NAME/KEY: misc_feature
<222> LOCATION: (5)..(5)
<223> OTHER INFORMATION: Xaa can be Phe or Tyr
<220> FEATURE:
<221> NAME/KEY: misc_feature
<222> LOCATION: (9)..(9)
<223> OTHER INFORMATION: Xaa can be Phe or Tyr

<400> SEQUENCE: 7

Xaa Lys Arg Lys Xaa Lys Arg Lys Xaa
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide: Histatin 5 16-mer

<400> SEQUENCE: 8

Gly Tyr Lys Arg Lys Phe His Glu Lys His His Ser His Arg Gly Tyr
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide: Reverse orientation histatin
      5 16-mer

<400> SEQUENCE: 9

Tyr Gly Arg His Ser His His Lys Glu His Phe Lys Arg Lys Tyr Gly
```

```
<210> SEQ ID NO 10
<211> LENGTH: 5
<212> TYPE: PRT
<213> ORGANISM: Artificial Sequence
<220> FEATURE:
<223> OTHER INFORMATION: Synthetic peptide: KM6
<220> FEATURE:
<221> NAME/KEY: misc_feature
<222> LOCATION: (1)..(5)
<223> OTHER INFORMATION: D-amino acids

<400> SEQUENCE: 10

Phe Lys Arg Lys Tyr
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide: KM7

<400> SEQUENCE: 11

Phe Lys Pro Lys Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide: KM8

<400> SEQUENCE: 12

Phe Lys Ser Lys Tyr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide: KM9

<400> SEQUENCE: 13

Phe Lys Arg Lys Phe
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide: KM10

<400> SEQUENCE: 14

Lys Phe Arg Tyr Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide: KM12 part 1
```

```
<400> SEQUENCE: 15

Tyr Lys Arg Lys Phe Cys
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide: KM12 part 2

<400> SEQUENCE: 16

Cys Phe Lys Arg Lys Tyr
1               5

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide: KM12 whole
<220> FEATURE:
<221> NAME/KEY: DISULFID
<222> LOCATION: (6)..(7)
<223> OTHER INFORMATION: di-sulfide linkage between the two cysteine
      residues

<400> SEQUENCE: 17

Tyr Lys Arg Lys Phe Cys Cys Phe Lys Arg Lys Tyr
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide: KM13

<400> SEQUENCE: 18

Cys Trp Lys Arg Lys Trp
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide: KM14 part 1

<400> SEQUENCE: 19

Trp Lys Arg Lys Trp Cys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide: KM14 part 2

<400> SEQUENCE: 20
```

```
Cys Trp Lys Arg Lys Trp
1               5

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide: KM14
<220> FEATURE:
<221> NAME/KEY: DISULFID
<222> LOCATION: (6)..(7)
<223> OTHER INFORMATION: di-sulfide linkage between the two cysteine
      residues

<400> SEQUENCE: 21

Trp Lys Arg Lys Trp Cys Cys Trp Lys Arg Lys Trp
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide: KM15

<400> SEQUENCE: 22

Phe Lys Cys Arg Lys Tyr
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide: KM17

<400> SEQUENCE: 23

Cys Phe Lys Arg Lys Tyr Cys
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide

<400> SEQUENCE: 24

Tyr Lys Arg Lys Phe
1               5
```